(12) United States Patent
Seo et al.

(10) Patent No.: US 11,452,586 B1
(45) Date of Patent: Sep. 27, 2022

(54) METHOD AND SYSTEM FOR MANAGING ANIMAL DATA

(71) Applicant: SB Solutions Inc., Ulsan (KR)

(72) Inventors: Seungup Seo, Ulsan (KR); Namhwan Sung, Ulsan (KR); Hae Dong Lee, Ulsan (KR); Seong Mun Kim, Ulsan (KR); Ji Woong Song, Ulsan (KR); Jagannath Malik, Ulsan (KR)

(73) Assignee: SB Solutions Inc., Ulsan (KR)

( * ) Notice: Subject to any disclaimer, the term of this patent is extended or adjusted under 35 U.S.C. 154(b) by 0 days.

(21) Appl. No.: 17/399,998

(22) Filed: Aug. 11, 2021

(30) Foreign Application Priority Data

Jun. 2, 2021 (KR) .................. 10-2021-0071307

(51) Int. Cl.
| | | |
|---|---|---|
| *A61D 17/00* | (2006.01) | |
| *A01K 11/00* | (2006.01) | |
| *A01K 29/00* | (2006.01) | |
| *A61B 10/00* | (2006.01) | |
| *A61B 5/11* | (2006.01) | |

(Continued)

(52) U.S. Cl.
CPC .......... *A61D 17/002* (2013.01); *A01K 11/006* (2013.01); *A01K 29/005* (2013.01); *A61B 5/0031* (2013.01); *A61B 5/11* (2013.01); *A61B 5/6801* (2013.01); *A61B 5/7267* (2013.01); *A61B 5/7275* (2013.01); *A61B 5/746* (2013.01); *A61B 10/0012* (2013.01);
(Continued)

(58) Field of Classification Search
CPC .. A61D 17/002; A01K 11/006; A01K 29/005; A61B 5/0031; A61B 5/11; A61B 5/6801; A61B 5/7267; A61B 5/7275; A61B 5/746; A61B 10/0012; A61B 2503/40; G16H 50/20; G16H 50/30
See application file for complete search history.

(56) References Cited

U.S. PATENT DOCUMENTS

| | | | |
|---|---|---|---|
| 7,878,149 B2 * | 2/2011 | Voronin ............... | A01K 29/005 |
| | | | 119/174 |
| 9,202,193 B2 * | 12/2015 | Kwak .................. | A01K 29/005 |

(Continued)

*Primary Examiner* — David J. McCrosky
(74) *Attorney, Agent, or Firm* — Christensen O'Connor Johnson Kindness PLLC (57) ABSTRACT

A method and system for managing animal data are disclosed. The system for managing animal data includes: a sensor inserted into the body of an animal or attached to the outside of the animal's body to provide an identifier of the animal; a first reader installed at a start portion of a passage through which the animal passes to receive the identifier of the animal from the sensor inserted into or attached to the animal when the animal moves past the start portion or the first reader and to identify a first time of receipt of the identifier; a second reader installed at an end portion of the passage to receive the identifier of the animal from the sensor inserted into or attached to the animal when the animal moves past the end portion or the second reader and to identify a second time of receipt of the identifier; and a management server that receives the identifier and the first time of receipt from the first reader, receives the identifier and the second time of receipt from the second reader, calculates the speed of movement of the animal matching the identifier, and predicting whether the animal matching the identifier is in estrus or not, based on the calculated speed of movement.

14 Claims, 7 Drawing Sheets

(51) Int. Cl.
  *A61B 5/00* (2006.01)
  *G16H 50/20* (2018.01)
  *G16H 50/30* (2018.01)
(52) U.S. Cl.
  CPC ............. *G16H 50/20* (2018.01); *G16H 50/30* (2018.01); *A61B 2503/40* (2013.01)

(56) References Cited

U.S. PATENT DOCUMENTS

| | | | | |
|---|---|---|---|---|
| 10,070,626 | B2 * | 9/2018 | Rovnyi | A61B 5/0022 |
| 10,244,736 | B2 * | 4/2019 | Song | A61D 17/002 |
| 10,849,314 | B2 * | 12/2020 | Genzow | A61B 7/003 |
| 2008/0270173 | A1 * | 10/2008 | Pratt | A01K 5/02 |
| | | | | 119/840 |
| 2011/0192356 | A1 * | 8/2011 | Loosveld | A01K 1/0023 |
| | | | | 119/840 |
| 2016/0029601 | A1 * | 2/2016 | Motoshima | G06Q 10/06 |
| | | | | 702/19 |
| 2019/0223412 | A1 * | 7/2019 | Jackson, III | A61B 5/725 |
| 2021/0319899 | A1 * | 10/2021 | Liu | G06K 9/6263 |

\* cited by examiner

METHOD AND SYSTEM FOR MANAGING ANIMAL DATA

CROSS-REFERENCES TO RELATED APPLICATIONS

This application is based on and claims priority under 35 U.S.C. 119 to Korean Patent Application No. 10-2021-0071307, filed on Jun. 2, 2021, in the Korean intellectual property office, the disclosures of which are herein incorporated by reference in their entireties.

TECHNICAL FIELD

The present disclosure relates to a method and system for managing animal data.

BACKGROUND OF THE INVENTION

There is growing interest in detecting estrus in livestock such as pigs, cattle, dogs, horses, and goats and predicting the right time for insemination. Correctly identifying the right time for insemination in livestock highly affects increases in pregnancy rates, that is, the profitability of livestock farms, so it is important to get the right time for insemination at an early stage.

Moreover, it is also very important to measure and manage information on livestock' body—for example, blood pressure, oxygen saturation, blood sugar, heart rate, and body temperature.

The above information is only for enhancement of understanding and therefore it may contain information that does not form part of the prior art that is known to a person of ordinary skill in the art.

SUMMARY

This summary is provided to introduce a selection of concepts in a simplified form that are further described below in the Detailed Description. This summary is not intended to identify key characteristics of the claimed subject matter, nor is it intended to be used as an aid in determining the scope of the claimed subject matter.

The present disclosure provides a method and system for managing animal data which are able to receive an identifier of an animal passing through a passage from a sensor inserted into the animal's body or attached to the outside of the animal's body via a first reader installed at a start portion of the passage and a second reader installed at an end portion of the passage, measure the speed of movement of the animal based on a first time of receipt of the identifier by the first reader and a second time of receipt of the identifier by the second reader, and measure whether the animal is in estrus or not based on the measured speed of movement.

The present disclosure provides a method and system for managing animal data which are able to further receive and manage information (e.g., blood pressure, oxygen saturation, blood sugar, heart rate, body temperature, etc.) on the animal's body measured via a sensor.

The present disclosure provides a method and system for managing animal data which are able to predict how the animal's health condition will change in the future and to give an alert ahead of time when the animal is expected to be at risk of a hypoglycemia shock, a decrease in oxygen saturation, a sudden change in heart rate, and abnormal body temperature.

An exemplary embodiment of the present disclosure provides a system for managing animal data, the system including: a sensor inserted into the body of an animal or attached to the outside of the animal's body to provide an identifier of the animal; a first reader installed at a start portion of a passage through which the animal passes to receive the identifier of the animal from the sensor inserted into or attached to the animal when the animal moves past the start portion or the first reader and to identify a first time of receipt of the identifier; a second reader installed at an end portion of the passage to receive the identifier of the animal from the sensor inserted into or attached to the animal when the animal moves past the end portion or the second reader and to identify a second time of receipt of the identifier; and a management server that receives the identifier and the first time of receipt from the first reader, receives the identifier and the second time of receipt from the second reader, calculates the speed of movement of the animal matching the identifier, and predicts whether the animal matching the identifier is in estrus or not, based on the calculated speed of movement.

According to one aspect, the management server may be configured to calculate the speed of movement of the animal when the animal passes through the passage, based on the time difference between the second time of receipt and the first time of receipt and the length of the passage.

According to another aspect, the management server may be configured to compare the calculated speed of movement with a preset threshold and generate an estrus notification signal if the calculated speed of movement is beyond the threshold.

According to yet another aspect, the management server may be configured to generate time-series data of the movement of speed by accumulating data of the calculated speed of movement and to predict whether the animal is in estrus or not by incorporating the generated time-series data of the speed of movement into a prediction model.

According to a further aspect, the time-series data of the speed of movement may be generated by accumulating movement speed measurements taken at preset time intervals in a two-dimensional array.

According to a further aspect, the prediction model may be trained in such a way as to take the time-series data of the speed of movement as input and produce a predicted time of estrus of the animal as output.

According to a further aspect, the sensor may be configured to collect information on an animal's body and generate and provide a health condition index, and at least one of the first and second readers is configured to the health condition index from the sensor and send the same to the management sever.

According to a further aspect, the management server may be configured to generate time-series data by accumulating values of the health condition index at constant time intervals, calculating a predicted value for the health condition index for some point in the future by incorporating the generated time-series data into a health condition index prediction model, compare the calculated predicted value for the health condition index with a preset threshold, and issue a risk alert signal if the calculated predicted value for the heath condition index is beyond the threshold.

According to a further aspect, the health condition index prediction model may be trained in such a way as to take time-series data accumulated over time as input and produce, as output, a predicted value for the health condition index for at least one point in the future subsequent to the time-series data.

According to a further aspect, the management server may be configured to determine that the calculated predicted value for the health condition index is beyond the preset threshold, if the calculated predicted value for the health condition index is below a preset lower threshold, if the calculated predicted value for the health condition index is above a preset upper threshold, or if the calculated predicted value for the health condition index is within a preset threshold range.

Another exemplary embodiment of the present disclosure provides a method for managing animal data by a computer device including at least one processor, the method including: receiving, by the at least one processor, an identifier of an animal and a first time of receipt of the identifier from a first reader installed at a start portion of a passage through which the animal passes, when the animal moves past the start portion or the first reader; receiving, by the at least one processor, the identifier of the animal and a second time of receipt of the identifier from a second reader installed at an end portion of the passage, when the animal moves past the end portion or the second reader; calculating, by the at least one processor, the speed of movement of the animal matching the identifier based on the first time of receipt and the second time of receipt; and predicting, by the at least one processor, whether the animal matching the identifier is in estrus or not based on the calculated speed of movement.

According to one aspect, in the calculating of the speed of movement, the speed of movement of the animal matching the identifier may be calculated based on the time difference between the second time of receipt and the first time of receipt and the length of the passage. According to another aspect, the predicting of whether the animal is in estrus or not may include: comparing the calculated speed of movement with a preset threshold; and generating an estrus notification signal if the calculated speed of movement is beyond the threshold.

According to yet another aspect, the predicting of whether the animal is in estrus or not may include: generating time-series data of the movement of speed by accumulating data of the calculated speed of movement; and predicting whether the animal is in estrus or not by incorporating the generated time-series data of the speed of movement into a prediction model.

According to a further aspect, the prediction model is trained in such a way as to take the time-series data of the speed of movement as input and produce a predicted time of estrus of the animal as output.

According to a further aspect, the method may further include receiving, by the at least one processor, a health condition index from at least one of the first and second readers, wherein the health condition index is generated based on information on the animal's body which is collected from a sensor inserted into the body of the animal or attached to the outside of the animal's body.

According to a further aspect, the method may further include: generating, by the at least one processor, time-series data by accumulating values of the health condition index at constant time intervals; calculating, by the at least one processor, a predicted value for the health condition index for some point in the future by incorporating the generated time-series data into a health condition index prediction model; comparing the calculated predicted value for the health condition index with a preset threshold; and issuing a risk alert signal if the calculated predicted value for the heath condition index is beyond the threshold.

It is possible to receive an identifier of an animal passing through a passage from a sensor inserted into the animal's body or attached to the outside of the animal's body via a first reader installed at a start portion of the passage and a second reader installed at an end portion of the passage, measure the speed of movement of the animal based on a first time of receipt of the identifier by the first reader and a second time of receipt of the identifier by the second reader, and measure whether the animal is in estrus or not based on the measured speed of movement.

Moreover, it is possible to further receive and manage information (e.g., blood pressure, oxygen saturation, blood sugar, heart rate, body temperature, etc.) on the animal's body measured via a sensor.

In addition, it is possible to predict how the animal's health condition will change in the future and to give an alert ahead of time when the animal is expected to be at risk of a hypoglycemia shock, a decrease in oxygen saturation, a sudden change in heart rate, and abnormal body temperature.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessive unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the gist of the embodiment unnecessarily vague.

Furthermore, in describing components of an embodiments, terms, such as a first, a second, A, B, (a), and (b), may be used. Such terms are used only to distinguish one component from the other component, and the essence, order, or sequence of a corresponding component is not limited by the terms. When it is said that one component is "connected", "combined", or "coupled" to the other component, the one component may be directly connected or coupled to the other component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

Figure 1:
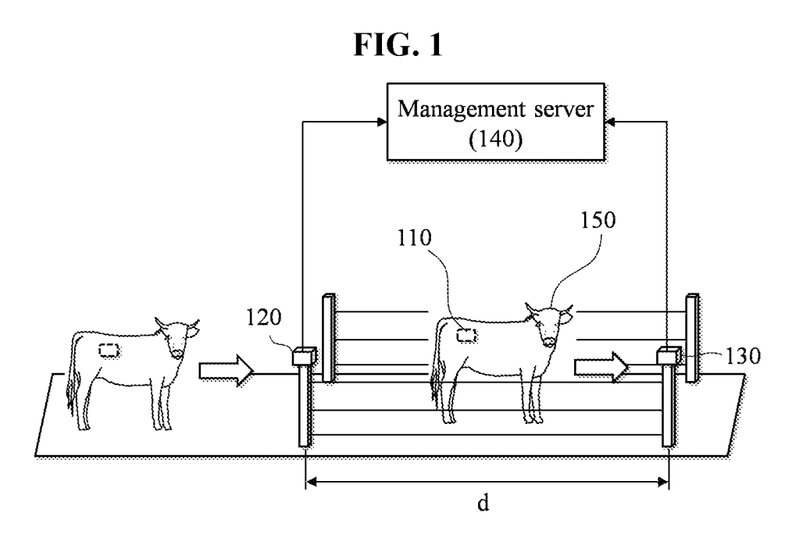
FIG. 1 is a view illustrating an example of a system for managing animal data according to an embodiment of the present disclosure.

FIG. 1 is a view illustrating an example of a system for managing animal data according to an embodiment of the present disclosure. The system for managing animal data according to this embodiment may include a sensor 110, a first reader 120, a second reader 130, and a management server 140.

The sensor 110 may be inserted into the body of an animal 150, which is a measurement target, or may be attached to the outside of the animal 150's body. In this instance, the sensor 110 may store an identifier of the animal 150, and may measure information on the animal 150's body (e.g., blood pressure, oxygen saturation, blood sugar, heart rate, and body temperature) from inside or outside the animal 150's body.

In this case, there may be a passage through which the animal 150 passes, and the first reader 120 and the second reader 130 may be installed at start and end portions of the passage, respectively. The first reader 120 and the second reader 130 may be configured to receive the identifier of the animal 150 from the sensor 110 of the animal 150 when the animal 150 passes through the passage. Communication between the first reader 120 and the sensor 110 and communication between the second reader 130 and the sensor 110 may be done via short-distance wireless communication. For example, radio frequency identification (RFID) may be used for, but not limited to, communication between the first reader 120 and the sensor 110 and communication between the second reader 130 and the sensor 110. Yet, communication may be done in such a way that the first reader 120 receives the identifier at a point in time when the animal 150 moves past the start portion of the passage (or the first reader 120) and the second reader 120 receives the identifier at a point in time when the animal 150 moves past the end portion of the passage (or the second reader 130). If necessary, a proximity sensor or pressure sensor may be used to identify points in time when the animal 150 moves past the start and end portions of the passage.

The first reader 120 may send a received identifier and a first time of receipt of the identifier to the management server 140. Similarly, the second reader 130 may send a received identifier and a second time of receipt of the identifier to the management server 140. The method of communication between the first reader 120 and second reader 130 and the management server 140 is not specifically limited and may include short-distance wireless communication between devices, as well as communication using a communication network (e.g., a mobile communication network, wired internet, wireless internet, and a broadcast network). For example, the first reader 120 and second reader 130 and the management server 140 may communicate over any one or more of networks including a personal area network (PAN), a local area network (LAN), a campus area network (CAN), a metropolitan area network (MAN), a wide area network (WAN), a broadband network (BBN), the Internet, and the like. Such networks can include, but is not limited to, any one or more of the following network topologies: a bus network, a star network, a ring network, a mesh network, a star-bus network, a tree or hierarchical network, and the like.

Meanwhile, the management server 140 may identify times when an animal 150 with a specific identifier enters the start portion of the passage and comes out of the end portion of the passage, based on the time difference between the second time of receipt and the first time of receipt. Moreover, the length d of the passage may be pre-inputted and stored in the management server 140. In this case, the management server 140 is able to know a distance and the amount of time taken for the animal 150 to move the distance, making it possible to calculate the speed of movement of the animal 150. The speed of movement may be calculated by dividing distance by time. For example, assuming that the length d of the passage is 5 m and the time calculated based on the time difference between the second time of receipt and the first time of receipt is 5s, the management server 140 may calculate the speed of movement of the animal 150 to be 1 m/s.

It is a well-known fact that animals 150 tend to move faster as they come into estrus. Accordingly, the management server 140 may predict whether an animal 150 matching an identifier is in estrus or not, based on the speed of movement of the animal.

In an embodiment, the management server 140 may be configured to compare the calculated speed of movement with a preset threshold and generate an estrus notification signal if the calculated speed of movement is beyond the threshold. The estrus notification signal may be outputted so as to be provided to the user of the animal data management system. Such an estrus notification signal may be outputted in the form of, but not limited to, sound, vibration, or light. For example, an estrus notification signal may be sent to the user's terminal in the form of an instant message.

In another embodiment, the management server 140 may predict whether the animal 150 is in estrus or not based on a prediction model. To this end, the management server 140 may be configured to generate time-series data of the speed of movement by accumulating data of the calculated speed of movement and to predict whether the animal 150 is in estrus or not by incorporating the generated time-series data of the speed of movement into a prediction model. The time-series data of the speed of movement may be generated by accumulating movement speed measurements taken at preset time intervals in a two-dimensional array. For example, the time-series data of the speed of movement may be generated by measuring the speed of movement of the animal 150 once a day by having the animal 150 pass through the passage where the first and second readers 120 and 130 are installed, and then accumulating daily measurements of the speed of movement in a two-dimensional array. The preset time intervals may be 1 day, or may be hour(s), week(s), month(s), etc. Meanwhile, the prediction model may be trained in such a way as to take the time-series data of the speed of movement as input and produce a predicted time of estrus of the animal as output.

Moreover, the sensor 110 may be configured to collect information on an animal's body and generate and provide a health condition index (HCI). In this case, at least one of the first and second readers 110 and 120 may be configured to collect the health condition index from the sensor 110 and send it to the management sever 140.

In this instance, the management server 140 may be configured to generate time-series data by accumulating values of the health condition index at constant time intervals, calculate a predicted value for the health condition index for some point in the future by incorporating the generated time-series data into a health condition index prediction model, compare the calculated predicted value for the health condition index with a preset threshold, and issue a risk alert signal if the calculated predicted value for the heath condition index is beyond the threshold. To this end, the management server 140 may generate time-series data for each health condition index by accumulating values of the health condition index in a two-dimensional array at constant time intervals. Here, the health condition index prediction model may be trained in such a way as to take time-series data accumulated over time as input and produce, as output, a predicted value for the health condition index for at least one point in the future subsequent to the time-series data.

As a more concrete example, the management server 140 may be configured to determine that the calculated predicted value of the health condition index is beyond the preset threshold, if the calculated predicted value for the health condition index is below a preset lower threshold, if the calculated predicted value for the health condition index is above a preset upper threshold, or if the calculated predicted value for the health condition index is within a preset threshold range. In this case, the management server 140 may issue a risk alert signal. The risk alert signal may be outputted in the form of, but not limited to, sound, vibration, or light. For example, the risk alert signal may be sent to the user's terminal in the form of an instant message.

Meanwhile, in some embodiments, at least some health condition indices may be additionally used, as well as the speed of movement, in order to predict whether the animal 150 is in estrus or not. For example, assuming that the sensor 110 measures five health condition indices for the animal 150, i.e., blood pressure, oxygen saturation, blood sugar, heart rate, and body temperature, at least one of the five health condition indices may be additionally used to predict whether the animal 150 is in estrus or not. For a more concrete example, if the animal 150 moves faster and its body temperature rises, it may be predicted with higher probability that the animal 150 is in estrus. For another example, if the animal 150 moves faster and its heart rate increases, it may be likewise predicted with higher probability that the animal 150 is in estrus.

Figure 2:
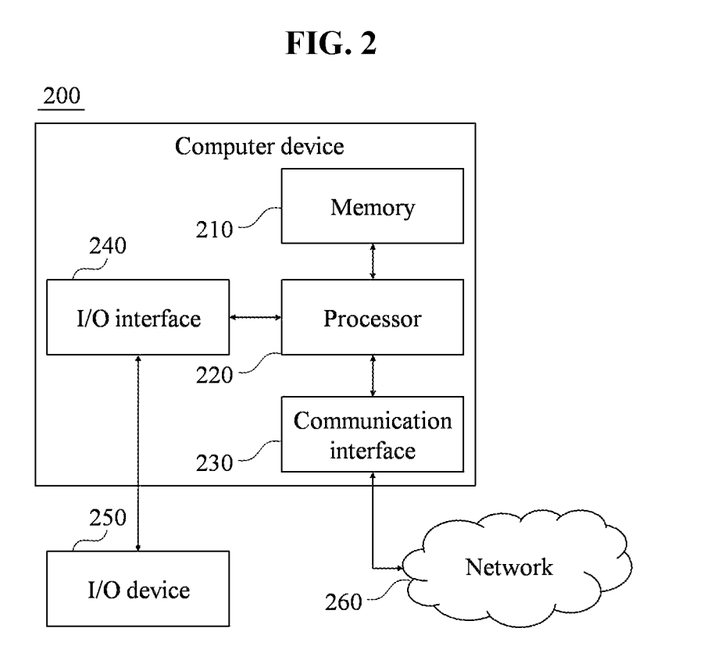
FIG. 2 is a block diagram illustrating an example of a computer device according to an embodiment of the present disclosure.

FIG. 2 is a block diagram illustrating an example of a computer device according to an embodiment of the present disclosure. For example, the above-described management server 140 may be implemented using the computer device 200 illustrated in FIG. 2.

As illustrated in FIG. 2, the computer device 200 may include a memory 210, a processor 220, a communication interface 230, and an I/O interface 240. The memory 210 is a computer-readable recording medium, and may include a permanent mass storage device such as a random access memory (RAM), a read only memory (ROM) and a disk drive. Here, the permanent mass storage device, such as a ROM and a disk drive, may be included in the computer device 200 as a permanent storage device separate from the memory 210. Moreover, an operating system and at least one program's code may be stored in the memory 210. Such software elements may be loaded onto the memory 210 from a computer-readable recording medium separate from the memory 210. Such a separate computer-readable recording medium may include computer-readable recording media, such as a floppy drive, a disk, a tape, a DVD/CD-ROM drive, and a memory card. In another embodiment, software elements may be loaded onto the memory 210, not via a computer-readable recording medium, but via the communication interface 230. For example, the software elements may be loaded onto the memory 210 of the computer device 200 based on a computer program installed by files received over a network 260.

The processor 220 may be configured to process instructions of a computer program by performing basic arithmetic, logic and I/O operations. The instructions may be provided to the processor 220 by the memory 210 or the communication interface 230. For example, the processor 220 may be configured to execute instructions received according to program code stored in a recording medium such as the memory 210.

The communication interface 230 may provide a function for enabling the computer device 200 to communicate with other devices over the network 260. For example, a request, a command, data or a file generated by the processor 220 of the computer device 200 according to program code stored in a recording device, such as the memory 210, may be sent to other devices over the network 260 under control of the communication interface 230. Inversely, a signal, a command, data or a file from another device may be received by the computer device 200 via the communication interface 230 of the computer device 200 over the network 260. A signal, a command, or data received via the communication interface 230 may be sent to the processor 220 or the memory 210, and a file received via the communication interface 230 may be stored in a storage medium (the aforementioned permanent storage device) which may be further included in the computer device 200.

The I/O interface 240 may be a means for interfacing with an input/output (I/O) device 250. For example, input devices such as a microphone, a keyboard, a camera, or a mouse may be included, and output devices such as a display or speaker may be included. For another example, the I/O interface 240 may be a means for interfacing with such a device as a touchscreen whose input and output functions are combined. The I/O device 250 may be integrated with the computer device 200.

Furthermore, in other embodiments, the computer device 200 may include more or fewer components than those shown in FIG. 2. However, it is not necessary to clearly illustrate most of conventional components. For example, the computer device 200 may be configured to include at least some of the above I/O devices 250, or may further include other components like a transceiver or a database.

Figure 3:
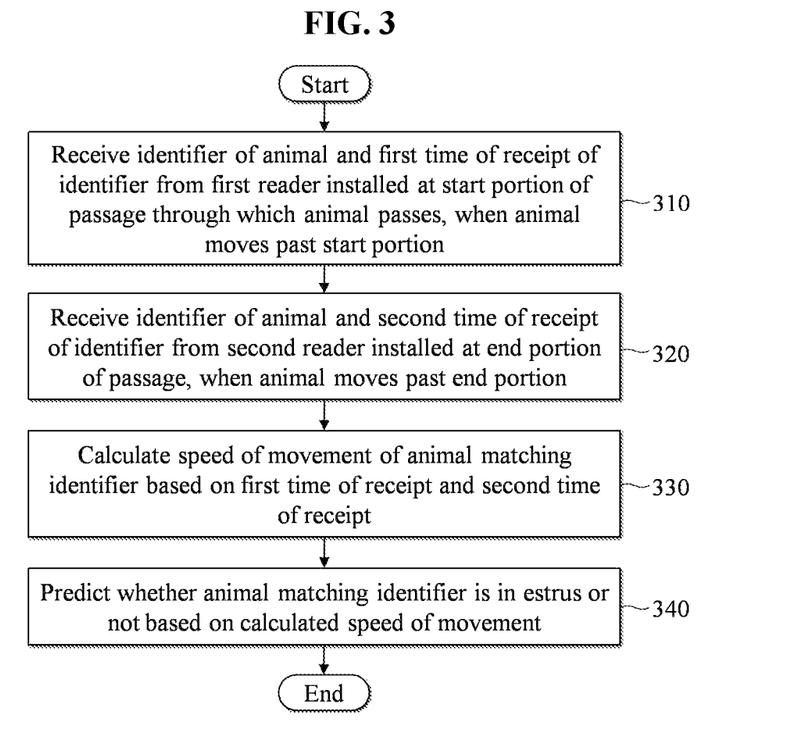
FIG. 3 is a flowchart illustrating an example of a method for managing animal data according to an embodiment of the present disclosure.

FIG. 3 is a flowchart illustrating an example of a method for managing animal data according to an embodiment of the present disclosure. The method for managing animal data according to this embodiment may be performed by a computer device 200 that implements a management server 140. The processor 220 of the computer device 200 may be configured to execute a control instruction according to code of an operating system included in the memory 210 or according to code of at least one computer program. Here, the processor 220 may control the computer device 200 in such a way that the computer device 200 performs the steps 310 to 340 included in the method of FIG. 3 in response to a control instruction provided by code stored in the computer device 200.

In the step S310, the computer device 200 may receive an identifier of an animal moving past a start portion of a passage and a first time of receipt of the identifier from a first reader installed at the start portion. Here, the first reader may correspond to the first reader 120 explained previously with reference to FIG. 1. The first reader is able to receive the identifier from a sensor (e.g., the sensor 110) inserted into the animal's body or attached to the outside of the animal's body, check the first time of receipt of the identifier, and send the identifier and the first time of receipt to the management server 140. At this point, the computer device 200 implementing the management server 140 is able to receive the identifier and the first time of receipt.

In the step 320, the computer device 200 may receive the identifier of the animal moving past an end portion of the passage and a second time of receipt of the identifier from a second reader installed at the end portion. Here, the second reader may correspond to the second reader 130 explained previously with reference to FIG. 1. The second reader is able to receive the identifier from a sensor (e.g., the sensor 110) inserted into the animal's body or attached to the outside of the animal's body, check the second time of receipt of the identifier, and send the identifier and the second time of receipt to the management server 140. At this point, the computer device 200 implementing the management server 140 is able to receive the identifier and the second time of receipt.

In the step 330, the computer device 200 may calculate the speed of movement of the animal matching the identifier based on the first time of receipt and the second time of receipt. For example, the computer device 200 may calculate the speed of movement of the animal matching the identifier based on the time difference between the second time of receipt and the first time of receipt and the length of the passage. It will be easily understood that, since the length of the passage is a distance, speed can be calculated based on time and distance.

In the step 340, the computer device 200 may predict whether the animal matching the identifier is in estrus or not based on the calculated speed of movement.

In an embodiment, the computer device 200 may compare the calculated speed of movement with a preset threshold, and, if the calculated speed of movement is beyond the threshold, may issue an estrus notification signal. As a more concrete example, if the speed of movement of an animal is above a preset threshold, the computer device 200 may issue an estrus notification signal for that animal. As explained previously, the estrus notification signal may be outputted via the computer device 200, or may be transmitted by the computer device 200 to another device and outputted via the another device.

In another embodiment, the computer device 200 may generate time-series data of the speed of movement by accumulating data of the calculated speed of movement and predict whether the animal is in estrus or not by incorporating the generated time-series data of the speed of movement into a prediction model. To this end, the computer device 200 may generate time-series data of the speed of movement by accumulating movement speed measurements taken at preset time intervals in a two-dimensional array. The prediction model may be trained in such a way as to take the time-series data of the speed of movement as input and produce a predicted time of estrus of the animal as output, and the computer device 200 may obtain the predicted time of estrus of the animal by incorporating the time-series data of the speed of movement into the trained prediction model. In this case, the computer device 200 may issue and provide an estrus notification signal at the predicted time of estrus of the animal.

In this way, it is possible to receive an identifier of an animal passing through a passage from a sensor inserted into the animal's body or attached to the outside of the animal's body via a first reader installed at a start portion of the passage and a second reader installed at an end portion of the passage, measure the speed of movement of the animal based on a first time of receipt of the identifier by the first reader and a second time of receipt of the identifier by the second reader, and measure whether the animal is in estrus or not based on the measured speed of movement.

Figure 4:
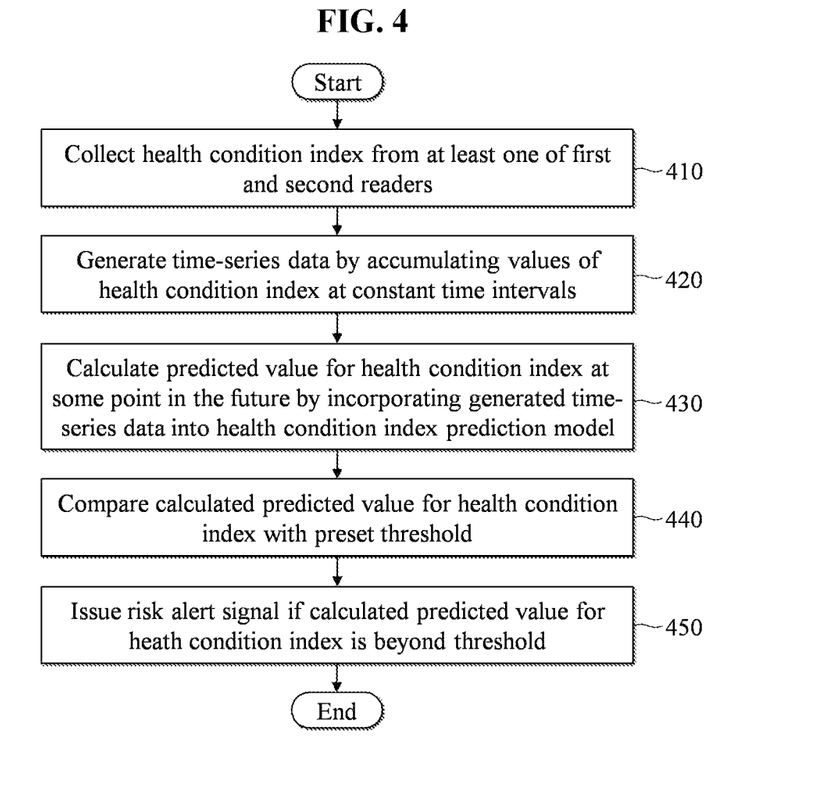
FIG. 4 is a flowchart illustrating another example of a method for managing animal data according to an embodiment of the present disclosure.

FIG. 4 is a flowchart illustrating another example of a method for managing animal data according to an embodiment of the present disclosure. The method for managing animal data according to this embodiment may be likewise performed by a computer device 200 that implements a management server 140. The processor 220 of the computer device 200 may be configured to execute a control instruction according to code of an operating system included in the memory 210 or according to code of at least one computer program. Here, the processor 220 may control the computer device 200 in such a way that the computer device 200 performs the steps 410 to 450 included in the method of FIG. 4 in response to a control instruction provided by code stored in the computer device 200.

In the step 410, the computer device 200 may collect a health condition index from at least one of the first and second readers. In this embodiment, a sensor may be configured to generate and provide a health condition index by collecting information on an animal's body. For example, a sensor may be configured to further transmit a health condition index to the first reader in addition to the identifier of the animal when the animal moves past the start portion of the passage (or the first reader 120) and/or to further transmit a health condition index to the second reader in addition to the identifier of the animal when the animal moves past the end portion of the passage (or the first reader 120). In this instance, the first reader and/or second reader receiving a health condition index may further transmit the health condition index to the management server 140 when transmitting the identifier and a time of receipt (first time of receipt and/or second time of receipt) to the management server 140. In the step 420, the computer device 200 may generate time-series data by accumulating values of the health condition index at constant time intervals. For example, the computer device 200 may generate time-series data for each health condition index by accumulating values of the health condition index in a two-dimensional array at constant time intervals. For example, when a sensor measures five health condition indices, i.e., blood pressure, oxygen saturation, blood sugar, heart rate, and body temperature, and transmits the five health condition indices (via the first reader and/or the second reader), the computer device 200 may generate time-series data for blood pressure, time-series data for oxygen saturation, time-series data for blood sugar, and time-series data for body temperature.

In the step 430, the computer device 200 may calculate a predicted value for the health condition index for some point in the future by incorporating the generated time-series data into a health condition index prediction model. Here, the health condition index prediction model may be trained in such a way as to take time-series data accumulated over time as input and produce, as output, a predicted value for the health condition index for at least one point in the future subsequent to the time-series data.

In the step 440, the computer device 200 may compare the calculated predicted value for the health condition index with a preset threshold. For example, the computer device 200 may determine that the calculated predicted value for the health condition index is beyond the preset threshold, if the calculated predicted value for the health condition index is below a preset lower threshold, if the calculated predicted value for the health condition index is above a preset upper threshold, or if the calculated predicted value for the health condition index is within a preset threshold range.

In the step 450, the computer device 200 may issue a risk alert signal if the calculated predicted value for the heath condition index is beyond the threshold. In this case, the computer device 200 may output a risk alert signal or transmit it to another device.

In this way, the computer device 200 may further receive and manage information (e.g., blood pressure, oxygen saturation, blood sugar, heart rate, body temperature, etc.) on the animal's body measured via a sensor, and may predict how the animal's health condition will change in the future and give an alert ahead of time when the animal is expected to be at risk of a hypoglycemia shock, a decrease in oxygen saturation, a sudden change in heart rate, and abnormal body temperature.

Figure 5:
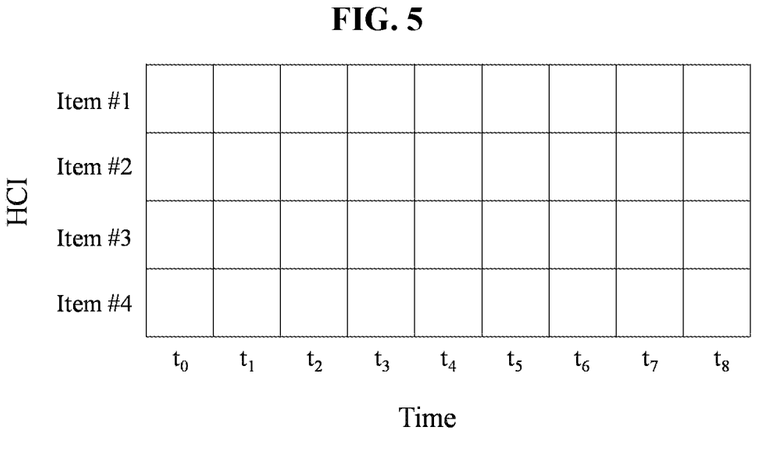
FIG. 5 is a view illustrating an example of time-series data according to an embodiment of the present disclosure.

FIG. 5 is a view illustrating an example of time-series data according to an embodiment of the present disclosure. FIG. 5 depicts an example in which a plurality of items of a health condition index are represented over time in a two-dimensional array.

Figure 6:
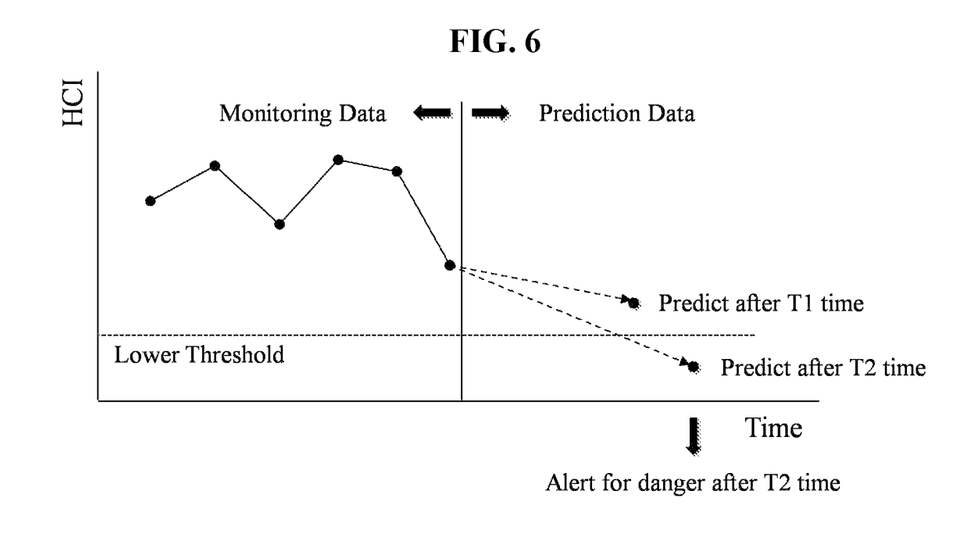
FIG. 6 is a view illustrating an example of prediction of a health condition index according to an embodiment of the present disclosure.

FIG. 6 is a view illustrating an example of prediction of a health condition index according to an embodiment of the present disclosure. The embodiment of FIG. 6 shows an example in which the management server 140 makes predictions of a health condition index for time T1 and time T2 by using collected data (e.g., time-series data of accumulated values of a health condition index which is received from the sensor 110 via the first reader 120 and/or the second reader 130). In this case, the predicted value for time T2 is below the lower threshold, and the management server 140 may therefore issue a risk alert signal and output the issued risk alert signal to the user or transmit it to another device.

Meanwhile, an artificial intelligence algorithm (e.g., a prediction model for outputting a predicted time of estrus and/or a health condition index prediction model) by which the management server 140 analyzes time-series data may be implemented using one or more of various algorithms including MLP (Multi-Layer Perceptron), DNN (Deep Neural Network), CNN(Convolutional Neural Network), RNN (Recurrent Neural Network), G-CNN (Group Convolutional Neural Network), and R-CNN(Recurrent Convolutional Neural Network), but is not limited to a particular algorithm.

For example, the management server 140 may create a health condition index (HCI) prediction model by training an artificial intelligence algorithm model by machine learning using training data. Machine learning may employ supervised learning or unsupervised learning, or may employ reinforcement learning during unsupervised learning. This is only an example, and the learning method is not limited to them.

Figure 7:
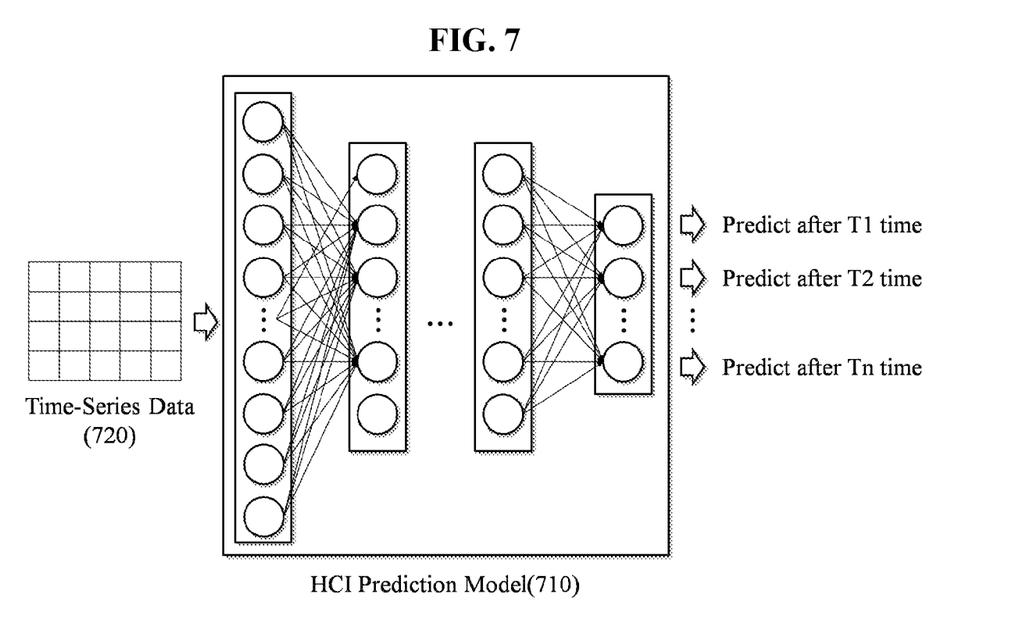
FIG. 7 is a conceptual diagram of predictions of a health condition index made by a health condition index prediction model according to an embodiment of the present disclosure.

FIG. 7 is a conceptual diagram of predictions of a health condition index made by a health condition index prediction model according to an embodiment of the present disclosure. Once time-series data 720 is fed, the HCI prediction model 710 may output predicted values for different points in times through a computation procedure within the HCI prediction model 710. Future points in time T1, T2, . . . , Tn for which the health condition index is to be predicted may be preset in a model selection process, and training data may be prepared accordingly. A prediction model may be created for only one point in time T1 as needed, or a prediction model may be created for multiple points in time as in the embodiment of FIG. 7.

According to these embodiments of the present disclosure, it is possible to receive an identifier of an animal passing through a passage from a sensor inserted into the animal's body or attached to the outside of the animal's body via a first reader installed at a start portion of the passage and a second reader installed at an end portion of the passage, measure the speed of movement of the animal based on a first time of receipt of the identifier by the first reader and a second time of receipt of the identifier by the second reader, and measure whether the animal is in estrus or not based on the measured speed of movement. Moreover, it is possible to further receive and manage information (e.g., blood pressure, oxygen saturation, blood sugar, heart rate, body temperature, etc.) on the animal's body measured via a sensor. In addition, it is possible to predict how the animal's health condition will change in the future and to give an alert ahead of time when the animal is expected to be at risk of a hypoglycemia shock, a decrease in oxygen saturation, a sudden change in heart rate, and abnormal body temperature.

Meanwhile, the sensor 110 may be configured to provide information on an animal's body, such as blood sugar and oxygen saturation, by including both a signal source that outputs a signal for measuring biological information and a detector that that detects reflected and returned signals. In this instance, the sensor 110 may include an oscillator-type sensing circuit, and the signal source and the detector may be included in such a sensing circuit.

In one embodiment, the sensor 110 may generate a fringing field, measure a change in a resonance frequency generated by an oscillator based on a change in capacitance caused by a change in an analyte in the fringing field area, and measure the characteristics of the change in the analyte in the fringing field, as the information on the animal's body, in response to the change in the resonance frequency.

As a more concrete example, the sensor 110 may generate a fringing field by a fringing-field capacitor of the oscillator which is included as the sensing circuit. Moreover, the sensor 110 may measure the characteristics of the change in the analyte within the fringing field in response to the change in the resonance frequency by measuring a change in capacitance caused by a change in permittivity by means of a sensing part including a material with a dielectric constant.

The sensing method using the oscillator-type sensing circuit is only an example for acquiring information on the animal's body but not limited thereto. For example, a light-based sensor may be used instead of the oscillator type to measure the animal's biological signals.

The aforementioned system or device may be implemented as a hardware component, a software component and/or a combination of a hardware component and a software component. For example, the device and components described in the embodiments may be implemented using one or more general-purpose computers or special-purpose computers, for example, a processor, a controller, an arithmetic logic unit (ALU), a digital signal processor, a microcomputer, a field programmable gate array (FPGA), a programmable logic unit (PLU), a microprocessor or any other device capable of executing or responding to an instruction. A processing device may perform an operating system (OS) and one or more software applications executed on the OS. Furthermore, the processing device may access, store, manipulate, process and generate data in response to the execution of software. For convenience of understanding, one processing device has been illustrated as being used, but a person having ordinary knowledge in the art may understand that the processing device may include a plurality of processing components and/or a plurality of types of processing components. For example, the processing device may include a plurality of processors or one processor and one controller. Furthermore, other processing configurations, such as a parallel processor, are also possible.

Software may include a computer program, a code, an instruction or a combination of one or more of them, and may configure a processor so that it operates as desired or may instruct processors independently or collectively. Software and/or data may be embodied in any type of a machine, component, physical device, virtual equipment, or computer storage medium or device so as to be interpreted by the processor or to provide an instruction or data to the processor. The software may be distributed to computer systems connected over a network and may be stored or executed in a distributed manner. The software and data may be stored in one or more computer-readable recording media.

The method according to the embodiment may be implemented in the form of a program instruction executable by various computer means and stored in a computer-readable recording medium. The computer-readable recording medium may include a program instruction, a data file, and a data structure alone or in combination. The program instructions stored in the medium may be specially designed and constructed for the present disclosure, or may be known and available to those skilled in the field of computer software. Examples of the computer-readable storage medium include magnetic media such as a hard disk, a floppy disk and a magnetic tape, optical media such as a CD-ROM and a DVD, magneto-optical media such as a floptical disk, and hardware devices specially configured to store and execute program instructions such as a ROM, a RAM, and a flash memory. Examples of the program instructions include not only machine language code that is constructed by a compiler but also high-level language code that can be executed by a computer using an interpreter or the like.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned components, such as the system, configuration, device, and circuit, are coupled or combined in a form different from that of the described method or replaced or substituted with other components or equivalents.

Accordingly, other implementations, other embodiments, and the equivalents of the claims fall within the scope of the claims.

The embodiments of the invention in which an exclusive property or privilege is claimed are defined as follows:

1. A system for managing animal data, the system comprising:
    a first sensor inserted into the body of an animal or attached to the outside of the animal's body to provide an identifier of the animal;
    a passage with a start portion and an end portion;
    a second sensor, selected from a proximity sensor or a pressure sensor, configured to identify points in time when the animal moves past the start portion and the end portion of a passage,
    wherein the first sensor is configured to collect information on an animal's body and generate and provide a health condition index, by generating a fringing field, measuring a change in resonance frequency based on a change in capacitance caused by a change in an analyte in the fringing field, and measuring the characteristics of the change in the analyte, in response to the change in resonance frequency;
    a first reader installed at the start portion of the passage through which the animal passes to receive the identifier of the animal from the first sensor inserted into or attached to the animal when the animal moves past the start portion or the first reader and to identify a first time of receipt of the identifier;
    a second reader installed at the end portion of the passage to receive the identifier of the animal from the first sensor inserted into or attached to the animal when the animal moves past the end portion or the second reader and to identify a second time of receipt of the identifier; and
    a management server that receives the identifier and the first time of receipt from the first reader, receives the identifier and the second time of receipt from the second reader, calculates the speed of movement of the animal matching the identifier, and predicts whether the animal matching the identifier is in estrus or not, based on the calculated speed of movement.

2. The system of claim 1, wherein the management server is configured to calculate the speed of movement of the animal when the animal passes through the passage, based on the time difference between the second time of receipt and the first time of receipt and the length of the passage.

3. The system of claim 1, wherein the management server is configured to compare the calculated speed of movement with a preset threshold and generate an estrus notification signal if the calculated speed of movement is beyond the threshold.

4. The system of claim 1, wherein the management server is configured to generate time-series data of the movement of speed by accumulating data of the calculated speed of movement and to predict whether the animal is in estrus or not by incorporating the generated time-series data of the speed of movement into a prediction model.

5. The system of claim 4, wherein the time-series data of the speed of movement is generated by accumulating movement speed measurements taken at preset time intervals in a two-dimensional array.

6. The system of claim 4, wherein the prediction model is trained in such a way as to take the time-series data of the speed of movement as input and produce a predicted time of estrus of the animal as output.

7. The system of claim 1, wherein at least one of the first and second readers is configured to collect the health condition index from the first sensor and send the same to the management server.

8. The system of claim 7, wherein the management server is configured to generate time-series data by accumulating values of the health condition index at constant time intervals, calculating a predicted value for the health condition index for some point in the future by incorporating the generated time-series data into a health condition index prediction model, compare the calculated predicted value for the health condition index with a preset threshold, and issue a risk alert signal if the calculated predicted value for the heath condition index is beyond the threshold.

9. A method for managing animal data by a computer device comprising at least one processor, the method comprising:
 detecting the presence of an animal entering a passage with a first sensor selected from a proximity sensor or a pressure sensor installed at a start portion of the passage;
 receiving, by the at least one processor, an identifier of an animal and a first time of receipt of the identifier from a first reader installed at the start portion of the passage through which the animal passes, when the animal moves past the start portion or the first reader;
 receiving, by the at least one processor, a health condition index from at least one of the first and second readers, wherein the health condition index is generated based on information on the animal's body which is collected from a second sensor configured to be inserted into the body of the animal or attached to the outside of the animal's body by:
  generating a fringing field,
  measuring a change in resonance frequency generated by an oscillator based on a change in capacitance caused by a change in an analyte in the fringing field area, and
  measuring the change in the analyte in the fringing field in response to the change in resonance frequency;
 detecting the presence of an animal leaving the passage with a third sensor selected from a proximity sensor or a pressure sensor installed at an end portion of the passage;
 receiving, by the at least one processor, the identifier of the animal and a second time of receipt of the identifier from a second reader installed at the end portion of the passage, when the animal moves past the end portion or the second reader;
 calculating, by the at least one processor, the speed of movement of the animal matching the identifier based on the first time of receipt and the second time of receipt; and
 predicting, by the at least one processor, whether the animal matching the identifier is in estrus or not based on the calculated speed of movement.

10. The method of claim 9, wherein, in the calculating of the speed of movement, the speed of movement of the animal matching the identifier is calculated based on the time difference between the second time of receipt and the first time of receipt and the length of the passage.

11. The method of claim 9, wherein the predicting of whether the animal is in estrus or not comprises:
 comparing the calculated speed of movement with a preset threshold; and
 generating an estrus notification signal if the calculated speed of movement is beyond the threshold.

12. The method of claim 9, wherein the predicting of whether the animal is in estrus or not comprises:
 generating time-series data of the movement of speed by accumulating data of the calculated speed of movement; and
 predicting whether the animal is in estrus or not by incorporating the generated time-series data of the speed of movement into a prediction model.

13. The method of claim 12, wherein the prediction model is trained in such a way as to take the time-series data of the speed of movement as input and produce a predicted time of estrus of the animal as output.

14. The method of claim 9, further comprising:
 generating, by the at least one processor, time-series data by accumulating values of the health condition index at constant time intervals;
 calculating, by the at least one processor, a predicted value for the health condition index for some point in the future by incorporating the generated time-series data into a health condition index prediction model;
 comparing the calculated predicted value for the health condition index with a preset threshold; and
 issuing a risk alert signal if the calculated predicted value for the heath condition index is beyond the threshold.

* * * * *